United States Patent
Kersbulck et al.

(10) Patent No.: US 8,580,984 B2
(45) Date of Patent: Nov. 12, 2013

(54) ESTERS OF SECONDARY HYDROXY FATTY ACID OLIGOMERS AND PREPARATION THEREOF

(75) Inventors: Jochem Kersbulck, Terneuzen (NL); Daniele Vinci, Ghent (BE); Johan A. Thoen, Antwerp (BE)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/378,059

(22) PCT Filed: Jul. 1, 2010

(86) PCT No.: PCT/US2010/040703
§ 371 (c)(1),
(2), (4) Date: Dec. 14, 2011

(87) PCT Pub. No.: WO2011/005635
PCT Pub. Date: Jan. 13, 2011

(65) Prior Publication Data
US 2012/0136168 A1    May 31, 2012

Related U.S. Application Data

(60) Provisional application No. 61/224,532, filed on Jul. 10, 2009.

(51) Int. Cl.
C09F 7/00    (2006.01)

(52) U.S. Cl.
USPC .............................. 554/26; 554/25

(58) Field of Classification Search
USPC ...................................... 554/25, 26
See application file for complete search history.

(56) References Cited

U.S. PATENT DOCUMENTS

| | | | |
|---|---|---|---|
| 2,396,994 A | 3/1946 | Filachione et al. | |
| 2,534,255 A | 12/1950 | Filachione et al. | |
| 2,580,460 A | * 1/1952 | Patton et al. | 524/306 |
| 2,652,410 A | 9/1953 | Cunningham et al. | |
| 2,721,188 A | 10/1955 | Polly et al. | |
| 3,278,459 A | 10/1966 | Herold | |
| 3,427,334 A | 2/1969 | Belner | |
| 3,941,849 A | 3/1976 | Herold | |
| 4,428,850 A | 1/1984 | Zoleski et al. | |
| 4,477,589 A | 10/1984 | van der Hulst et al. | |
| 4,684,473 A | 8/1987 | Bock et al. | |
| 4,699,998 A | 10/1987 | Green | |
| 5,011,629 A | * 4/1991 | Bilbo | 554/122 |
| 5,158,922 A | 10/1992 | Hinney et al. | |
| 5,237,080 A | 8/1993 | Daute et al. | |
| 5,374,366 A | 12/1994 | Nakahara et al. | |
| 5,380,894 A | 1/1995 | Burg et al. | |
| 5,420,315 A | 5/1995 | Uhrig et al. | |
| 5,427,704 A | 6/1995 | Lawate | |
| 5,442,082 A | 8/1995 | Uphues et al. | |
| 5,451,332 A | 9/1995 | Lawate | |
| 5,458,795 A | 10/1995 | Lawate | |
| 5,470,813 A | 11/1995 | Le-Khac | |
| 5,482,908 A | 1/1996 | Le-Khac | |
| 5,731,407 A | 3/1998 | Le-Khac | |
| 5,856,413 A | 1/1999 | Charles et al. | |
| 6,018,063 A | 1/2000 | Isbell et al. | |
| 6,201,144 B1 | 3/2001 | Isbell et al. | |
| 6,316,649 B1 | 11/2001 | Cermak et al. | |
| 6,362,265 B1 | * 3/2002 | Wo et al. | 524/315 |
| 6,407,272 B1 | 6/2002 | Nelson et al. | |
| 6,429,324 B1 | 8/2002 | Raths et al. | |
| 7,348,460 B2 | 3/2008 | Wulff et al. | |
| 2002/0017629 A1 | 2/2002 | Mosier et al. | |

(Continued)

FOREIGN PATENT DOCUMENTS

| | | |
|---|---|---|
| EP | 1712576 A1 | 10/2006 |
| EP | 1842866 A1 | 10/2007 |

(Continued)

OTHER PUBLICATIONS

Cermak S C et al: "Synthesis and physical properties of estolides from lesquerelta and castor fatty acid esters" Industrial Crops and Products, vol. 23, No. 1, Jan. 1, 2006, pp. 54-64.*
Swern, Daniel et al: "Viscosity characteristics of esters of hydroxystearic acids" Journal of Chemical and Engineering Data, vol. 5, pp. 231-233, 1960.*
Previtera L et al: "Fatty acid composition in Lemna minorcharacterization of a novel hydroxy C16 acid" Phytochemistry, vol. 22, No. 6, Jan. 1, 1983, pp. 1445-1446.*
Gunstone F D et al: "Fatty acids, part 37—Application of the oxymercuration-demercuration reaction to long-chain unsaturated esters" Chemistry and Physics of Lipids, vol. 10, No. 1, Jan. 1, 1973.*

(Continued)

Primary Examiner — Deborah D Carr
(74) Attorney, Agent, or Firm — Steven W. Mork

(57) ABSTRACT

Prepare an ester of a secondary hydroxy fatty acid oligomer by first partially homopolymerizing a hydroxylated fatty acid compound, reacting the partially homopolymerized hydroxylated fatty acid compound with an alcohol to form an intermediate product, and capping the intermediate product with an acid, acid anhydride or ester. The ester of a secondary hydroxy fatty acid oligomer may be represented as follows: (3) where R is an alkyl group that contains from six to twelve carbon atoms, $R^1$ is hydrogen or a methyl radical, x is an integer within a range of from 8 to 12, n is an integer between 1 and 20, $R^2$ is an alkyl group that contains from one carbon atom to twenty carbon atoms and $R^3$ is an alkyl group that contains from one carbon atom to twelve carbon atoms.

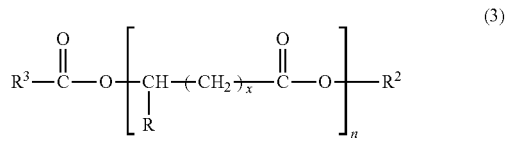

(3)

9 Claims, 1 Drawing Sheet

(56) References Cited

U.S. PATENT DOCUMENTS

Figure 1:
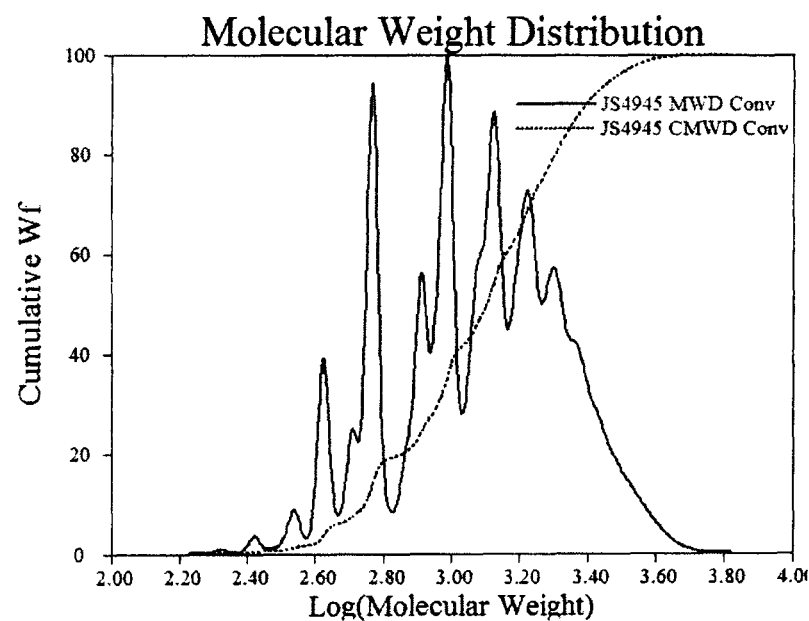

| | | | |
|---|---|---|---|
| 2005/0014908 A1 | 1/2005 | Kutsuna et al. |
| 2007/0123725 A1 | 5/2007 | Lorenz |
| 2008/0175931 A1 | 7/2008 | Schlemer et al. |
| 2011/0213170 A1 | 9/2011 | Vinci et al. |
| 2011/0269980 A1 | 11/2011 | Vinci et al. |

FOREIGN PATENT DOCUMENTS

| | | | |
|---|---|---|---|
| FR | 2290414 | | 11/1974 |
| FR | 2290414 A1 | * | 6/1976 |
| FR | 2374290 | | 12/1976 |
| FR | 2374290 A1 | * | 7/1978 |
| JP | 5163342 A | | 6/1993 |
| JP | 7228881 | | 8/1995 |
| JP | 8027473 | | 3/1996 |
| JP | 10036870 | | 2/1998 |
| WO | 01/53247 A1 | | 7/2001 |
| WO | 2006047436 A1 | | 5/2006 |
| WO | 2008/040864 A1 | | 4/2008 |
| WO | 2008124265 A2 | | 10/2008 |
| WO | 2009139003 A1 | | 11/2009 |
| WO | 2011005635 A1 | | 1/2011 |
| WO | 2011037778 A1 | | 3/2011 |
| WO | 2013002910 A1 | | 6/2011 |
| WO | 2011106186 A1 | | 9/2011 |

OTHER PUBLICATIONS

Frankel, Edwin N. et al: "Oxidative acetoxylation of methyl oleate with palladium catalysts" Journal of Organic Chemistry, 40(22), 1975.*

S.C. Cermak, et al., "Synthesis and Physical Properties of Estolides from Lesquerella and Castor Fatty Acid Esters", Industrial Crops and Producs, vol. 23, No. 1, Jan. 1, 2006.

Daniel Swern, et al., "Viscosity Characteristics of Esters of Hydroxystearic Acids", Journal of Chemical and Engineering Data, p. 232, Table 1, 1960.

L. Previtera, et al., "Fatty Acid Composition in Lemna Minor-Characterization of a Novel Hydroxy C16 Acid", Phytochemistry, vol. 22, No. 6, Jan. 1, 1983.

F.D. Gunstone, et al., "Fatty Acids, part 37—Application of the Oxymercuration-demercuration Reaction to Long-Chain Unsaturated Esters", Chemistry and Physics of Lipids, vol. 10, No. 1, Jan. 1, 1973.

Edwin N. Frankel, et al., "Oxidative Acetoxylation of Methyl Oleate with Palladium Catalysts", Journal of Organic Chemistry, vol. 40, No. 22, 1975.

Sharma, et al., "Chemical Modification of Vegetable Oils for Lubricant Applications", Journal of the Americal Oil Chemists' Society, 2006, vol. 83, No. 2, pp. 129-136.

Cermak et al., "Synthesis and Physical Properties of Tallow-Oleic Estolide 2-Ethylhexyl Esters", Journal of the American Oil Chemists' Society, 2007, vol. 84, pp. 449-456.

Cermak et al., "Synthesis and physical properties of mono-estolides with varying chain lengths", Industrial Crops and Products, 2009, vol. 29, No. 1, pp. 205-213, Elsevier.

International Search Report and Written Opinion for PCT/US2010/040703 dated Sep. 21, 2010.

International Search Report and Written Opinion for PCT/US2011/024702 dated May 17, 2011.

International Search Report and Written Opinion for PCT/US2011/031497 dated Aug. 9, 2011.

International Search Report and Written Opinion for PCT/US2012/038565 dated Aug. 3, 2012.

* cited by examiner

ESTERS OF SECONDARY HYDROXY FATTY ACID OLIGOMERS AND PREPARATION THEREOF

CROSS REFERENCE TO RELATED APPLICATIONS

This application is a 35 USC §371 national phase filing of PCT/US2010/040703 filed Jul. 1, 2010, which claims the benefit of U.S. Application No. 61/224,532, filed Jul. 10, 2009.

This application is a non-provisional application claiming priority from the U.S. Provisional Patent Application No. 61/224,532, filed on Jul. 10, 2009, entitled "ESTERS OF SECONDARY HYDROXY FATTY ACID OLIGOMERS AND PREPARATION THEREOF," the teachings of which are incorporated by reference herein, as if reproduced in full hereinbelow.

This invention relates to a process for preparing esters of secondary hydroxy fatty acid oligomers, especially a double ester of a 12-hydroxy stearic acid based oligomer, which double ester is at least substantially free of residual unsaturation, and uses thereof, particularly as a lubricant composition component.

Natural esters (for example, canola oil) and synthetic esters can be used to formulate bio-lubricants that conform to the requirements of the European Eco-label (European Commission 2005/360/EC). These formulations must contain certain minimum levels of renewable carbon atoms in the formulation. As an example, hydraulic fluids require a minimum level of renewable carbons of at least (>) 50 percent.

Formulations containing synthetic esters offer higher lubricant performance than vegetable oil based products but do so at a significantly higher cost. Synthetic esters can be derived from petrochemical or renewable feedstocks. For example, many short chain acids (for example, hexanoic, octanoic and decanoic acid) are produced from petrochemical feed stocks and used in preparing synthetic polyol esters. Other acids, such as oleic acid are derived from renewable feed stocks.

Unsaturated fatty acid (for example, oleic acid) polyol esters based on polyfunctional alcohols such as neopentylglycol (NPG), pentaerythritol (PAE) or trimethylolpropane (TMP), especially TMP trioleate or NPG dioleate, currently find favor as base fluids for formulating biolubricants that need to conform with the European Eco-label criteria. Such polyol esters have a high renewable carbon content (at or above European Eco-label criteria) and have low pour points (less than (<) −25° centigrade (° C.). However they also contain a high degree (for example, >10 grams of iodine per 100 gram, ASTM D5554) of unsaturation (olefinic moieties in the acid fraction of the esters) and this leads to oxidation when the lubricants are used in high temperature (for example, greater than or equal to (≥) 90° C.) equipment. For such equipment, users prefer saturated polyol esters, but such esters are sufficiently expensive that users desire lower cost alternatives without sacrificing high temperature performance.

Compositions that constitute or comprise high oleic vegetable oils (for example, genetically-modified or high oleic canola oil) also have high renewable carbon content but can also undergo oxidative breakdown under some conditions. For example, lubricants formulated with a high level of vegetable oil (>50 percent) are not recommended for use in high temperature equipment where the lubricant bulk fluid temperature is >90° C. This can lead to undesirable changes in viscosity, acidity or both and consequent loss of desirable physical or chemical properties such as pour point and thermo-oxidative stability.

A desire exists for an improved lubricant composition based upon renewable materials, also known as a "bio-lubricant composition". The improved composition should have one or more of a low pour point (for example, a pour point <−10° C.) and acceptable thermo-oxidative stability (that is, when the improved composition includes an antioxidant, it should exhibit a kinematic viscosity change of no more than (≤) 20 percent (percent) using a modified American Society for Testing and Materials (ASTM) D2893 test in which the test modification is a change in temperature from 95° C. to 120° C.). The improved composition should also meet lubricating or viscosity requirements for industrial lubricants, automotive lubricants or both (for example, a viscosity at 40° C. within a range of from 10 centistokes (cSt ($1\times10^{-5}$ meters squared per second ($m^2/s$)) to, 300 cSt ($3\times10^{-4}$ $m^2/s$), a viscosity at 100° C. within a range of from 4 centistokes ($4\times10^{-6}$ $m^2/s$) to, 50 centistokes ($5\times10^{-5}$ $m^2/s$) and a viscosity index (VI) >140). The improved composition preferably lacks a distribution of unsaturation, such as that found in estolides, which tend to adversely affect thermo-oxidative stability of the estolides.

Figure 2:
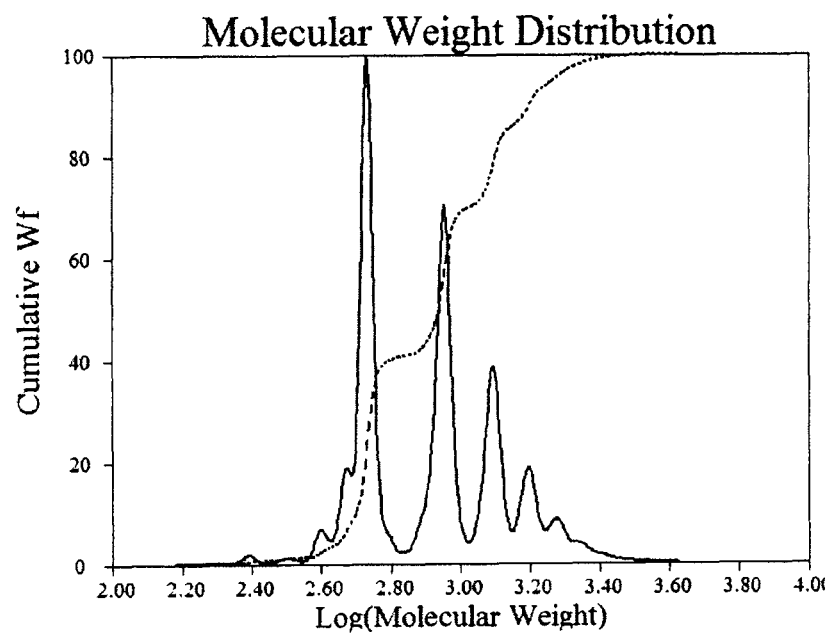

FIGS. 1 and 2 illustrate gel permeation chromatography traces for final products of Ex 18 and Ex 2, respectively.

An "estolide" is an oligomeric fatty acid formed by condensation of two or more fatty acid units to yield an ester linkage. One typically achieves condensation by adding a carboxylic acid moiety onto a double bond via acid catalysis.

U.S. Pat. No. 6,018,063 (Isbell et al.) relates to esters of estolides derived from oleic acids. Isbell et al. describes typical synthesis of estolides as involving homopolymerization of castor oil fatty acids or 12-hydroxystearic acid under thermal or acid catalyzed conditions.

U.S. Pat. No. 6,407,272 (Nelson et al.) teaches preparation of secondary alcohol esters of hydroxy acids (for example, ricinoleate esters of secondary alcohols) by reacting an ester of a hydroxy acid with a secondary alcohol in the presence of an organometallic transesterification catalyst.

Patent Cooperation Treaty Publication (WO) 2008/040864 relates to a method for synthesizing estolide esters having a "high and controlled" oligomerization level and a low residual acid index. The method involves simultaneous oligomerization of a saturated hydroxy acid and esterification of the hydroxyacid by a monoalcohol.

In some aspects, this invention is a process for preparing an ester of a secondary hydroxy fatty acid oligomer, the process comprising:

a. partially homopolymerizing a hydroxylated fatty acid compound, using a tin-containing, titanium-containing or nitrogen-containing catalyst and removing formed methanol, optionally by using one or more of an entrainer, reduced pressure, and nitrogen sparging, to yield a product X with distribution of compounds represented by Formula 1 as follows:

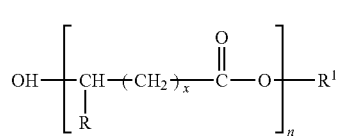

Formula 1 where R is an alkyl group that contains from six to twelve carbon atoms, $R^1$ is hydrogen or a methyl radical; x is an integer within a range of from 8 to 12 and n is an integer between 1 and 20.

b. optionally recovering product X from residual methanol and, when used, the entrainer;

c. reacting product X with an alcohol that contains from two to twenty carbon atoms, optionally using an additional amount of a tin-containing, titanium-containing or nitrogen-containing catalyst, and removing formed methanol to yield a product Y with distribution of compounds represented by Formula 2 as follows:

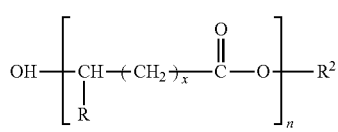

Formula 2 where R, x and n are as defined above and $R^2$ is an alkyl group that contains from one carbon atom to twenty carbon atoms;

d. optionally recovering product Y from excess step c alcohol and residual methanol;

e. reacting product Y with an acid, an acid anhydride or an ester to form product Z with a distribution of compounds represented by Formula 3 as follows:

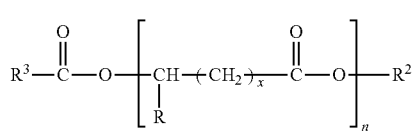

Formula 3 where R, x and n are as defined above, $R^2$ is an alkyl group that contains from one carbon atom to twenty carbon atoms and $R^3$ is an alkyl group that contains from one carbon atom to twelve carbon atoms and f. optionally recovering product Z from excess acid, acid anhydride or ester added as a reactant in step e and acid formed during reaction of Y with the acid, acid anhydride or ester.

In some aspects, this invention is an ester of a secondary hydroxy fatty acid oligomer represented by Formula 3 above. The ester preferably has at least one of a pour point less than $-10°$ C., a VI greater than or equal to ($\geq$) 160, and a total acid number <1 mg KOH/g. In some aspects, the ester has a hydroxyl number (OH#) less than or equal to ($\leq$) 10, preferably <8, more preferably <5, still more preferably <4 and even more preferably <3.

In Formulae 1, 2 and 3 above, R is a six carbon ($C_6$) to twelve carbon ($C_{12}$) alkyl group or moiety, with a $C_6$ moiety being preferred, and n is an integer that ranges from 8 to 12, with 10 being preferred. In Formula 1 above, $R^1$ is a hydrogen atom or a methyl group or moiety. In Formulae 2 and 3 above, $R^2$ is a $C_2$ to $C_{20}$ alkyl group or moiety with a $C_8$ (2-ethylhexyl) moiety being preferred for Formulae 2 and 3. In Formula 3 above, $R^3$ is a $C_1$ to $C_{12}$ alkyl group or moiety with a $C_4$ moiety being preferred.

The above process comprises three steps. In step one, oligomerize a hydroxylated fatty acid component, preferably a methyl ester of a 12-hydroxy fatty acid and more preferably a methyl ester of 12-hydroxy stearic acid, using a tin (Sn), titanium (Ti), or nitrogen-based catalyst to yield an oligomer that has more than one repeating unit and an unreacted fatty acid component concentration that is <90 percent by weight (wt percent), based upon total oligomer structure weight. Step one occurs without use of an acid catalyst. In step two, react, preferably quantitatively, the oligomer with an alcohol that has from two carbon atoms ($C_2$) to 20 carbon atoms ($C_{20}$). The alcohol preferably has from six carbon atoms ($C_6$) to 16 carbon atoms ($C_{16}$), more preferably from 8 ($C_8$) carbon atoms to ten ($C_{10}$) carbon atoms. Illustrative alcohols include 2-ethylhexanol, 2-(2-butoxypropoxy)propan-1-ol (DPnB), 1 octanol and 2-octanol. In step three, cap remaining hydroxy-functional groups with an acid, an acid anhydride or an ester, preferably an acid anhydride of Formula 4 as follows:

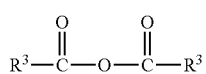

Formula 4 where $R^3$ is as defined above. Illustrative anhydrides include isobutyric anhydride.

Oligomer unreacted fatty acid component concentration has, as its converse, degree of condensation. That is an unreacted fatty acid component concentration of <90 wt percent equates to a condensation of more than (>) 10 wt percent, with unreacted fatty acid component concentration and condensation, when taken together, equating to 100 wt percent. Condensation preferably ranges from 10 wt percent to 95 wt percent, more preferably from 15 wt percent to 85 wt percent and still more preferably from 20 wt percent to 75 wt percent, to achieve a VI greater than (>) 160 and pour point lower than (<) $-10°$ C.

Step a. optionally, but preferably, includes use of an entrainer or compound that facilitates removal of methanol before reacting product X with a $C_2$-$C_{20}$ alcohol. Methanol removal, during step a, is beneficial because it drives oligomerization beyond the equilibrium point, which allows one to make products with higher viscosities than one can obtain at or below the equilibrium point.

Step a. occurs at a temperature sufficient to effect partial homopolymerization or condensation, within ranges noted above, of the hydroxylated fatty acid compound and azeotropic distillation of methanol formed during reaction and, when used, the entrainer. The temperature is preferably within a range of from $70°$ C. to $220°$ C., more preferably from $120°$ C. to $210°$ C., and still more preferably from $180°$ C. to $200°$ C.

Step c. occurs at a temperature sufficient to effect 1) a reaction between product X and a $C_2$-$C_{20}$ alcohol and 2) removal of methanol formed during the reaction by fractional distillation to yield product Y. The temperature is preferably within a range of from 70 degrees $°$ C. to $220°$ C., more preferably from $120°$ C. to $210°$ C., and still more preferably from $180°$ C. to $200°$ C. The $C_2$-$C_{20}$ alcohol is preferably present in an amount sufficient to provide at least one molar equivalent of alcohol for each molar equivalent of X.

Step e. occurs at a temperature sufficient to effect a reaction between product Y and an acid, acid anhydride or ester to form product Z. The temperature is preferably within a range of from 80 degrees $°$ C. to $160°$ C., more preferably from $100°$ C. to $140°$ C., and still more preferably from $110°$ C. to $130°$ C.

Optional step b., recovering product X from residual methanol formed during step a and, when used, an entrainer occurs via conventional procedures such as azeotropic distillation with the entrainer, preferably an aliphatic compound having from 7 carbon atoms ($C_7$) to 10 carbon atoms ($CO_{10}$), most preferably 9 carbon atoms (C₉). Entrainer and residual methanol and entrainer removal preferably occurs via distillation under reduced pressure (for example, 4 kilopascals (kPa)). The temperature is preferably within a range of from 100° C. to 200° C., more preferably from 120° C. to 190° C., and still more preferably from 150° C. to 180° C.

Optional step d., recovering product Y from excess step c. alcohol and residual methanol from step b. occurs via conventional procedures such as fractionated distillation. Step d. preferably involves distillation under reduced pressure (for example, 4 kPa) to effect recovery of product Y. The temperature is preferably within a range of from 70° C. to 350° C., more preferably from 120° C. to 250° C., and still more preferably from 150° C. to 180° C.

Optional step f., recovering product Z from excess acid, acid anhydride or ester added as a reactant in step e and acid formed during reaction of product Y with the acid, acid anhydride or ester, preferably includes one or more of 1) use of reduced pressure to remove volatile materials, 2) washing one or more times with a base such as an aqueous solution of sodium hydrogen carbonate (NaHCO₃), 3) use of absorbent materials such as magnesium silicate, activated carbon and magnesium sulfate (MgSO₄), and 4) filtration.

Arabic numerals and capital alphabetic letters designate, respectively, examples (Ex) of the invention and comparative examples (CEx).

EX 1

For step one, use a 1 liter (L) glass reactor equipped with a temperature controller, an overhead stirrer, an electric heater and a Dean-Stark apparatus with water condenser connected to a vacuum/nitrogen line, add 968.22 grams (g) (3.1 moles) of methyl-12-hydroxystearate (M12HSA), 150 grams of nonane and 3.25 g (0.5 mole percent (mol percent), based upon moles of M12HSA) tin(II)-2-ethylhexanoate to form a mixture. Heat the mixture to a set point temperature of 200° C. and maintain that temperature with stirring for a period of four hours (hrs), removing methanol via azeotropic distillation with nonane. Total methanol collection amounts to 52 g (1.6 moles), equating to 54 percent condensation or 46 percent remaining methyl ester functionality yielding a product with a distribution of compounds represented by Formula 5 as follows:

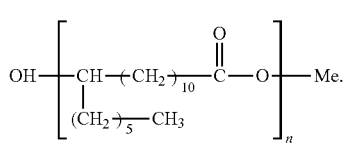

Formula 5

For step two, remove remaining nonane under reduced pressure and cool reactor contents to a set point temperature of 135° C. Place a vigreaux distillation column between the reactor and the Dean-Stark apparatus, then add 303.56 g (2.3 moles) of 2-ethylhexanol (2-EH) and 3.25 g (0.008 mole) of tin(II)dioctoate to the reactor and heat reactor contents, with stirring, to a set point temperature of 190° C. for six hours. Remove methanol formed during step two (36.3 g, 1.13 moles) from reactor contents by fractional distillation.

For step three, subject reactor contents to distillation under reduced pressure (50 kPa) to remove residual methanol not removed via fractional distillation and excess 2-ethylhexanol, to yield a product with a distribution of compounds represented by Formula 6 as follows:

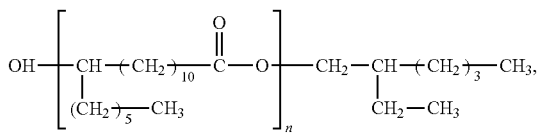

Formula 6 then cool reactor contents to a set point temperature of 130° C. and add 220.5 g (1.52 moles) of isobutyric anhydride to the reactor and stir reactor contents for two hours. Remove excess isobutyric anhydride and acid formed during capping with the isobutyric anhydride under reduced pressure. Maintain reduced pressure for two hours, then cool reactor contents to a set point temperature of 70° C. and add 100 milliliters (mL) of a 0.5 molar (M) sodium hydrogen carbonate (NaHCO₃) in water solution to the reactor with stirring. Maintain the set point temperature with stirring for one hour, then remove water under reduced pressure. Add 10 g of magnesium silicate, 5 g of activated carbon and 10 g of magnesium sulfate (MgSO₄) to the reactor, then filter the reactor contents using a filter paper coated with 80 g of magnesium silicate to yield a final product with a distribution of compounds represented by Formula 7 as follows:

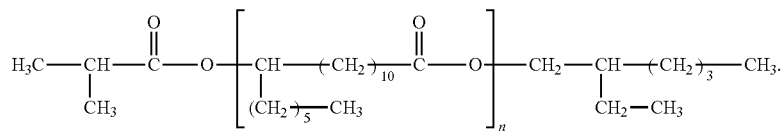

Formula 7

Table 1 below summarizes physical property information for methyl-12-hydroxystearate (M12HSA), an intermediate product (following reaction with the 2-ethylhexanol) and the final product (following reaction with isobutyric anhydride).

TABLE 1

| Physical Property/material | M12HSA | Intermediate Product | Final Product |
|---|---|---|---|
| Viscosity @ 40° C. (centistokes) | 127* | 94 | 54.3 |
| Viscosity @ 100° C. (centistokes) | 15.4* | 12.2 | 9.81 |
| Viscosity Index | 126 | 123 | 168 |
| Pour Point (° C.) | >20 | >0 | −14 |
| Total Acid Number (mg KOH/g) | 0.09 | 0.16 | 0.04 |
| Water content (wt percent) | 0.024 | 0.017 | 0.026 |
| OH# (mg KOH/g) | 79.0 | 82.6 | <3 |

*value reported in megapascals per second (mPa/s)

The data in Table 1 demonstrate that step one allows one to build a certain molecular weight (degree of oligomerization or condensation) in the final product as indicated by a decrease of OH# from 171 milligrams of potassium hydroxide per gram (mgKOH/g) (OH# of M12HSA) to 79.0 mg KOH/g of product X (column heading "M12HSA"). Proceeding from step 1 (column heading "M12HSA") through step 3 (column heading "Final Product"), one obtains a gradual decrease in viscosity and pour point, as well as an increase in VI. Step 3 also results in an OH# lower than (<) 3 mg KOH/g, an indication that the Final Product has a very low hydroxyl moiety content which favors thermo-oxidative stability relative to higher hydroxyl moiety contents such as 79 mg KOH/g. The washing step has no influence on viscosity or VI, but it does significantly reduce Total Acid Number (TAN).

EX 2

Replicate Ex 1 with changes to reduce M12HSA condensation to 43 percent. For step one, increase M12HSA content to 5449.1 g, reducing tin(II)dioctoate to 0.25 mol percent, reducing temperature to 190° C. and increasing time to six hours. For step two, add 0.5 mol percent tin(II)-2-ethylhexanoate, increasing time to 62 hours, using 2905.3 g of product from step one and increasing the amount of 2-EH to 1212.3 g. For step three, use 2702.77 g of product from step two, increase amount of isobutyric anhydride to 982.2 g and reduce temperature to 125° C. Summarize final product properties in Table 2 below.

EX 3

Replicate Ex 2, but change 2-EH to 1-octanol in an amount of 656 g, reduce the amount of tin (II) ethylhexanoate to 0.25 mol percent for step two, change the amount of step one product used in step two to 1475 g, change the step two time to 7 hours, reduce the amount of isobutyric anhydride in step three to 390 g, change the amount of step two product used in step three to 1668.21 g, reduce the step three temperature to 120° C. and increase step three time to 3 hours.

CEx A

Replicate Ex 2, but eliminate step two, use 687.35 g of product from step one in step three, substitute 372.58 g of methyl decanoate (C10ME) for isobutyric anhydride and move addition of the 0.25 mol percent of tin(II)-2-ethylhexanoate to step three. In addition, change the step three temperature to 210° C. and time to 22 hours.

CEx B

Replicate Ex 2, but eliminate steps two and three, use 920 g of M12HSA, increase M12HSA condensation to 60 percent and change step one conditions to 210° C. for 6 hours.

EX 4

Replicate Ex 1, but use 941.4 g of M12HSA, split the tin(II)2-ethylhexanoate addition equally between steps one and two, change the condensation in step one to 47 percent, substitute 493.0 g of 2-(2-butoxypropoxy)propan-1-ol (DPnB) for 2-EH and use 757.39 g of product from step one in step two, and use respective steps one, two and three combinations of temperature and time as follows: 190° C. for three hours, 215° C. for 26 hours and 125° C. for two hours.

EX 5

Replicate Ex 2, but change step one M12HSA condensation to 51 percent, change the amount of M12HSA to 5994.4 g, split the tin(II)2-ethylhexanoate addition as in Ex 4, use 2387.5 g of step one product and 988.9 g of 2-EH in step two, and use respective steps one, two and three combinations of temperature and time as follows: 190° C. for 12 hours, 190° C. for 35 hours and 125° C. for two hours.

EX 6

Replicate Ex 5, but use 1654 g of step one product, reduce the amount of tin(II)2-ethylhexanoate addition to 0.24 mol percent and substitute 612 g of 1-octanol for the 2-EH, all in step two. In step three, react 1802.89 g of step two product and 415 g of isobutyric anhydride.

EX 7

Replicate Ex 2, but change the amount of M12HSA to 6079.7 g and step one conditions to 187 C and 15 hours, change the amount of 2-EH to 2285.9 g and the amount of tin(II)2-ethylhexanoate in step two to 0.25 mol percent, use 5621.7 g of step one product in step two, change step two time to 35 hours, and change the amount of isobutyric anhydride to 1573.4 g.

EX 8

Replicate Ex 7 but substitute 315 g of acetic anhydride for the isobutyric anhydride and use 1682.8 g of product from step two rather than 4608.5 g as in Ex 7 and change step three temperature to 120° C. Summarize final product properties in Table 3 below.

EX 9

Replicate Ex 7, but use 6061.2 g of M12HSA, 0.24 mol percent of tin(II)2-ethylhexanoate, a temperature of 190° C., a time of 4 hours and reduce M12HSA condensation to 29 percent in step one. In step 2, use 662.9 g of product from step one and 413.12 g of 2-EH and reduce time at temperature to 24 hours. In step three, use 897.87 g of product from step two and 382.1 g of isobutyric anhydride.

EX 10

Replicate Ex 9, but use 4972.84 g of M12HSA, change step one time to 285 minutes and change M12HSA condensation to 34 percent. In step two, use 688.96 g of step one product, 317.6 g of 2-EH and change step two time to 23 hours. In step three, use 764.4 g of step two product, 235.5 g of isobutyric anhydride and increase step three time to 4 hours.

EX 11

Replicate Ex 9, but use 2677.7 g of M12HSA, change step one time and temperature to 193° C. and 435 minutes and change M12HSA condensation to 43 percent. In step two, use 658.59 g of step one product, 280.5 g of 2-EH and change step two time to 20 hours. In step three, use 688.19 g of step two product and 208.74 g of isobutyric anhydride.

EX 12

Replicate Ex 9, but use 945.2 g of M12HSA, change step one time and temperature to 195° C. and 900 minutes and change M12HSA condensation to 60 percent. In step two, use 887.9 g of step one product, 275.65 g of 2-EH and change step two time to 23 hours. In step three, use 931.17 g of step two product and 274.4 g of isobutyric anhydride.

EX 13

Replicate Ex 7, but use 5210.3 g of M12HSA, change step one time and temperature to 200° C. and 6.5 hours and change M12HSA condensation to 46 percent. In step two, use 4860.6 g of step one product, 2159.8 g of 2-EH and change step two time to 16 hours and temperature to 190° C. In step three, use 5636.1 g of step two product, 1271.3 g of isobutyric anhydride and change step three temperature to 130° C.

EX 14

Replicate Ex 13, but use 5239.84 g of M12HSA, change step one time and temperature to 190° C. and 16 hours and change M12HSA condensation to 47 percent. In step two, use 1352.53 g of step one product, 619.1 g of 2-EH and change step two time to 22 hours and temperature to 190° C. In step three, use 1789.0 g of step two product and 495.4 g of isobutyric anhydride.

EX 15

Replicate Ex 14, but use 902.53 g of M12HSA, change step one time and temperature to 200° C. and 22 hours and change M12HSA condensation to 70 percent. In step two, use 758.62 g of step one product, 184.65 g of 2-EH and change step two time to 16 hours. In step three, use 841.41 g of step two product, 168.59 g of isobutyric anhydride and effect the NaHCO$_3$ wash in a step four at 70° C. for 2 hours.

EX 16

Replicate Ex 15, but use 5064 g of M12HSA, change step one time and temperature to 190° C. and 10 hours and change M12HSA condensation to 44 percent. In step two, use 4741.71 g of step one product, 2147.6 g of 2-EH and change step two time to 22 hours. In step three, use 5467.21 g of step two product and 1517.1 g of isobutyric anhydride. Change step four temperature to 65° C. for 2 hours. Summarize final product properties in Table 4 below.

EX 17

Replicate Ex 16, but use 5036 g of M12HSA, change step one time to 9 hours and change M12HSA condensation to 47 percent. In step two, use 4710.88 g of step one product, 1693.5 g of 2-EH and change step two time to 19 hours. In step three, use 50292.07 g of step two product and 1693.5 g of isobutyric anhydride and change the temperature to 120° C.

CEx C

Replicate Ex 17, but eliminate condensation, effectively combining steps one and two to react 706 g of M12HSA with 296 g of 2-EH at 190° C. for 6 hours. In step three, react 348 g of isobutyric anhydride with 866.3 g of product from combined steps one and two.

EX 18

Replicate Ex 1, but change the amount of M12HSA to 963.45 g and condensation in step one to 54 percent. In step two, use 825.48 g of product from step one and substitute 364 g of 2-octanol for 2-EH and change step two time and temperature to 20 hours at 200° C. In step three, use all of the product from step two and 220.25 g of isobutyric anhydride.

CEx D

Replicate Ex 18, but eliminate condensation, effectively combining steps one and two to react 593.8 g of M12HSA with 449.7 g of 2-octanol at 185° C. for 17 hours. In step three, react 188.13 g of isobutyric anhydride with 712.58 g of product from combined steps one and two at a temperature of 135° C.

EX 19

Replicate Ex 18, but change the amount of M12HSA to 956.72 g and condensation in step one to 72 percent. In step two, use 821.92 g of product from step one and substitute 250 g of 1-octanol for 2-EH and change step two time to 16 hours. In step three, use 946.9 g of product from step two and a slight excess of isobutyric anhydride.

EX 20

Replicate Ex 19, but change the amount of M12HSA to 971 g and condensation in step one to 53 percent. In step two, use 836 g of product from step one and 364.1 g of 1-octanol and change step two time to 20 hours. In step three, use 903.2 g of product from step two and 220.4 g of isobutyric anhydride.

CEx E

Replicate Ex 18, but eliminate condensation, effectively combining steps one and two to react 393.3 g of M12HSA with 329.5 g of 1-octanol at 195° C. for 17 hours. In step three, react 188.13 g of isobutyric anhydride with 443.48 g of product from combined steps one and two at a temperature of 130° C.

TABLE 2

| Physical Property/Ex or CEx | Ex 2 | Ex 3 | CEx A | CEx B | Ex 4 | Ex 5 | Ex 6 | Ex 7 |
|---|---|---|---|---|---|---|---|---|
| Viscosity @ 40° C. (centistokes) | 40.5 | 39.1 | 101 | 42.3 | 62.9 | 55.9 | 50.8 | 48.1 |
| Viscosity @ 100° C. (centistokes) | 7.89 | 7.85 | 16.6 | 8.11 | 11.3 | 10.1 | 9.66 | 9.0 |
| Viscosity Index | 170 | 177 | 178 | 169 | 175 | 171 | 179 | 171 |
| Pour Point (° C.) | −20 | −7 | | | −20 | | | |
| Total Acid Number (mg KOH/g) | 0.03 | 0.10 | 0.36 | 0.07 | 0.47 | 0.04 | 0.08 | 0.05 |
| Water content (wt %) | 0.036 | 0.017 | 0.034 | 0.061 | 0.035 | 0.014 | 0.013 | 0.017 |
| OH# (mg KOH/g) | <3 | 6.9 | <3 | 10.4 | <3 | <3 | <3 | <3 |

TABLE 3

| Physical Property/Ex or CEx | Ex 8 | Ex 9 | Ex 10 | Ex 11 | Ex 12 | Ex 13 | Ex 14 | Ex 15 |
|---|---|---|---|---|---|---|---|---|
| Viscosity @ 40° C. (centistokes) | 51.7 | 26.5 | 31.3 | 40.3 | 67.6 | 46.8 | 44.9 | 102 |
| Viscosity @ 100° C. (centistokes) | 9.29 | 5.78 | 6.5 | 7.88 | 11.76 | 8.76 | 8.58 | 16.3 |
| Viscosity Index | 164 | 170 | 168 | 171 | 171 | 169 | 172 | 171 |
| Pour Point (° C.) | −18 | | | | | −16 | −18 | −21 |
| Total Acid Number (mg KOH/g) | 0.13 | 1.9 | 0.59 | 0.14 | 0.27 | 0.05 | 0.15 | 0.07 |
| Water content (wt %) | 0.008 | 0.029 | | | 0.016 | | | |
| OH# (mg KOH/g) | <3 | <3 | <3 | <3 | 3.17 | 7.95 | <3 | 3.67 |

TABLE 4

| Physical Property/Ex or CEx | Ex 16 | Ex 17 | CEx C | Ex 18 | CEx D | Ex 19 | Ex 20 | CEx E |
|---|---|---|---|---|---|---|---|---|
| Viscosity @ 40° C. (centistokes) | 41.6 | 43.3 | 19.3 | 82.8 | 24.5 | 75.3 | 47.8 | 16.8 |
| Viscosity @ 100° C. (centistokes) | 8.08 | 8.35 | 4.52 | 13.8 | 5.27 | 13.1 | 9.2 | 4.25 |
| Viscosity Index | 171 | 172 | 155 | 171 | 187 | 177 | 178 | 169 |
| Pour Point (° C.) | −18 | −15 | −12 | | | −13 | −20 | 2 |
| Total Acid Number (mg KOH/g) | 0.11 | 0.07 | 0.05 | 0.81 | 0.35 | 0.31 | 0.92 | 0.33 |
| Water content (wt %) | 0.036 | 0.033 | 0.058 | 0.102 | 0.043 | 0.034 | 0.034 | 0.035 |
| OH# (mg KOH/g) | 2.11 | <3 | <3 | <3 | 14.6 | 3.71 | <3 | <3 |

The data suggest that choice of alcohol in step two makes a difference in final product properties. For example, a comparison of Ex 2 (2-ethylhexanol) and Ex 4 (DPnB) with Ex 3 (1-octanol) shows a noticeable increase in pour point. Ex 18 (2-octanol) also shows how carrying out step two to a lesser extent than other Ex, as a result of a secondary alcohol being less reactive than a primary alcohol, affects final product properties. See gel permeation chromatography (GPC) traces for final products of Ex 18 and Ex 2 as reproduced in FIGS. 1 and 2, respectively, for a visual comparison wherein Ex 18 has a higher level of a distribution of unreacted methyl ester components than Ex 2.

A comparison among Ex 2, CEx B and Ex 13, all of which use 2-ethyl hexanol, shows that incomplete capping (step three) results in final product OH # >3 which appears to be associated with higher viscosities and lower VI values.

Ex 2, CEx A and Ex 8 show impact of capping agent upon final product properties. For example, only a small difference in viscosity results in a switch between isobutyric anhydride (Ex 2) and acetic anhydride (Ex 8). CEx A, which uses C 10ME as a capping agent, shows a substantially higher viscosity than either Ex 2 or Ex 8, an indication that capping is incomplete even after a step three time of 22 hours.

Ex 2, Ex 5, Ex 7-12, Ex 14-17 and Ex 19 show effects of varying extent of M12HSA oligomerization or condensation in step one. These Ex appear to show a final product with higher viscosities, higher VI values and lower pour points than one can obtain without oligomerization as in CEx C.

A comparison of final product properties among Ex 2, Ex 6, CEx C, CEx D, Ex 20 and CEx E shows how product properties change between a three step process with an amount of condensation in step one (Ex 2, Ex 6 and Ex 20) and a two step process with no condensation (CEx C, CEx D and CEx E). For example, pour point temperatures are lower and viscosity at both 40° C. and 100° C. is higher for Ex 2, Ex 6 and Ex 20 than they are for CEx C, CEx D and CEx E. CEx C, CEx D and CEx E also tend to have lower viscosities than Ex 2, Ex 6 and Ex 20.

What is claimed is:

1. A process for preparing an ester of a secondary hydroxy fatty acid oligomer, the process comprising:

a. partially homopolymerizing a hydroxylated fatty acid methyl ester, using a tin-containing, titanium-containing or nitrogen-containing catalyst and removing formed methanol, optionally by using one or more of an entrainer, reduced pressure and nitrogen sparging, to yield a product X with distribution of compounds represented by Formula 1 as follows:

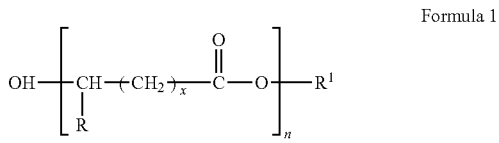

Formula 1 where R is an alkyl group that contains from six to twelve carbon atoms, $R^1$ is hydrogen or a methyl radical, x is an integer within a range of from 8 to 12 and n is an integer between 1 and 20;

b. optionally recovering product X from residual methanol and, when used, the entrainer;

c. reacting product X with an alcohol that contains from two to twenty carbon atoms, optionally using an additional amount of a tin-containing, titanium-containing or nitrogen-containing catalyst, and removing formed methanol to yield a product Y with distribution of compounds represented by Formula 2 as follows:

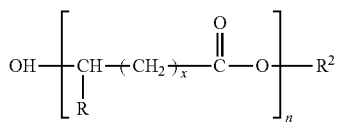

Formula 2 where R, x and n are as defined above and $R^2$ is an alkyl group that contains from two carbon atoms to twenty carbon atoms;

d. optionally recovering product Y from excess step c alcohol and residual methanol;

e. reacting product Y with an acid, an acid anhydride or an ester to form product Z with a distribution of compounds represented by Formula 3 as follows:

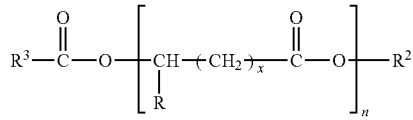

Formula 3 where R, x and n are as defined above, $R^2$ is an alkyl group that contains from two carbon atoms to twenty carbon atoms and $R^3$ is an alkyl group that contains from one carbon atom to twelve carbon atoms; and f. optionally recovering product Z from excess acid, acid anhydride or ester added as a reactant in step e and acid formed during reaction of Y with the acid, acid anhydride or ester.

2. The process of claim 1, wherein the catalyst is a tin catalyst.

3. The process of claim 1, wherein step a. effects homopolymerization of at least 10 wt percent, but no more than 95 wt percent of the hydroxylated fatty acid methyl ester.

4. The process of claim 1, wherein alcohol is present in step c. in an amount sufficient to provide at least one molar equivalent of alcohol for each molar equivalent of X.

5. The process of claim 1, wherein product Y reacts with an acid anhydride in step e.

6. The process of claim 1, wherein the hydroxylated fatty acid methyl ester is methyl 12-hydroxystearate.

7. The process of claim 1, wherein the alcohol in step c is selected from 2-ethylhexanol, 1-octanol and 2-octanol.

8. An ester of a secondary hydroxy fatty acid oligomer represented by formula 3 as follows:

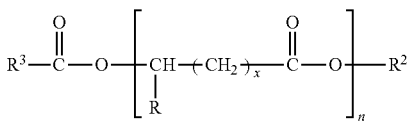

Formula 3 where R is an alkyl group that contains from six to twelve carbon atoms, x is an integer within a range of from 8 to 12, n is an integer between 1 and 20, $R^2$ is an alkyl group that contains from two carbon atoms to twenty carbon atoms and $R^3$ is an alkyl group that contains from one carbon atom to twelve carbon atoms;

wherein the ester of Formula 3 is prepared according to claim 1.

9. The ester of claim 8, wherein the ester has at least one of a pour point less than −10° centigrade, a viscosity index greater than or equal to 160, a hydroxyl number of less than 8, and a total acid number lower than 1 mg KOH/g.

* * * * *